United States Patent
Jensen

Patent Number: 6,071,528
Date of Patent: Jun. 6, 2000

[54] ADHESIVE ANTIMICROBIAL AND/OR REPARATIVE DENTIN STIMULATING DENTAL COMPOSITIONS AND METHODS FOR FORMING AND USING SUCH COMPOSITIONS

[75] Inventor: Steven D. Jensen, Riverton, Utah

[73] Assignee: Ultradent Products, Inc., South Jordan, Utah

[21] Appl. No.: 08/803,602

[22] Filed: Feb. 19, 1997

[51] Int. Cl.[7] ................................................. A01N 25/24
[52] U.S. Cl. ........................ 424/407; 424/405; 424/406; 424/409; 424/434; 424/435; 424/487; 424/722; 513/109; 513/122
[58] Field of Search .................................. 424/722, 487, 424/405–409, 421, 422, 434, 435; 523/109, 122

[56] References Cited

U.S. PATENT DOCUMENTS

| | | |
|---|---|---|
| 3,882,600 | 5/1975 | Plymale ........................ 32/15 |
| 3,997,504 | 12/1976 | Plymale ........................ 260/42.27 |
| 4,222,780 | 9/1980 | Shibatani et al. .............. 106/35 |
| 4,259,075 | 3/1981 | Yamauchi et al. ............. 433/217 |
| 4,259,117 | 3/1981 | Yamauchi et al. ............. 106/35 |
| 4,368,043 | 1/1983 | Yamauchi et al. ............. 433/217 |
| 4,385,153 | 5/1983 | Ritter ............................ 524/522 |
| 4,442,239 | 4/1984 | Tsunekawa et al. ........... 523/116 |
| 4,499,251 | 2/1985 | Omura et al. .................. 526/278 |
| 4,515,930 | 5/1985 | Omura et al. .................. 526/276 |
| 4,525,493 | 6/1985 | Omura et al. .................. 523/116 |
| 4,537,940 | 8/1985 | Omura et al. .................. 526/278 |
| 4,539,382 | 9/1985 | Omura et al. .................. 526/276 |
| 4,612,384 | 9/1986 | Omura et al. .................. 558/198 |
| 4,650,847 | 3/1987 | Omura et al. .................. 526/376 |
| 4,657,941 | 4/1987 | Blackwell et al. ............. 522/14 |
| 4,669,983 | 6/1987 | Bunker ........................... 433/217.1 |
| 4,670,576 | 6/1987 | Bunker ........................... 558/182 |
| 4,806,381 | 2/1989 | Engelbrecht et al. .......... 427/2 |
| 4,813,876 | 3/1989 | Wang .............................. 433/244 |
| 4,814,423 | 3/1989 | Huang et al. ................... 528/230 |
| 4,816,495 | 3/1989 | Blackwell et al. ............. 522/14 |
| 4,872,936 | 10/1989 | Engelbrecht ................... 156/307.3 |
| 4,929,746 | 5/1990 | Bunker ........................... 558/92 |
| 4,966,934 | 10/1990 | Huang et al. ................... 524/315 |
| 5,055,497 | 10/1991 | Okada et al. ................... 523/116 |
| 5,089,051 | 2/1992 | Eppinger et al. ............... 106/35 |
| 5,141,560 | 8/1992 | Combe et al. .................. 106/35 |
| 5,177,121 | 1/1993 | Bunker ........................... 523/116 |
| 5,192,815 | 3/1993 | Okada et al. ................... 523/115 |
| 5,243,006 | 9/1993 | Nakabayashi et al. ......... 526/286 |
| 5,264,513 | 11/1993 | Ikemura et al. ................ 526/318 |
| 5,306,338 | 4/1994 | Tsunekawa ..................... 106/35 |
| 5,338,773 | 8/1994 | Lu et al. ......................... 523/116 |
| 5,367,002 | 11/1994 | Huang et al. ................... 523/116 |
| 5,378,785 | 1/1995 | Mitra .............................. 526/316 |
| 5,554,669 | 9/1996 | Nakabayashi et al. ......... 523/118 |
| 5,558,517 | 9/1996 | Shalaby et al. ................. 433/201.1 |

FOREIGN PATENT DOCUMENTS

| | | |
|---|---|---|
| 60-045510 | 3/1985 | Japan. |
| 61-151104 | 7/1986 | Japan. |
| 95170479 | 7/1995 | Japan. |

OTHER PUBLICATIONS

McAplur Abstract #125:96183 Kyokawa et al—JP08099811, Apr. 1996.
McAplur—#123:17984 Komura et al JP—07082115, Mar. 1995.
Merchant et al pp 122, 123, 1967.

*Primary Examiner*—Neil S. Levy
*Attorney, Agent, or Firm*—Workman, Nydegger & Seeley

[57] ABSTRACT

Adhesive antimicrobial dental compositions and methods for forming and using compositions are disclosed. The compositions are primarily useful as pulp caps and dentin liners. The composition includes an alkyl methacrylate having an oxyphosphorus group, a polymerization initiator and an antimicrobial agent. The antimicrobial agent can be organohalogens, antibiotics, alkali metal hydroxides, alkaline earth metal oxides and alkaline earth metal hydroxides. The compositions have high dentin tensile bond strength, are stable as a single component or package system, can be polymerized in situ, prevent ingress by microorganisms into an area of a tooth treated with the compositions and can be syringe delivered.

16 Claims, 1 Drawing Sheet

ADHESIVE ANTIMICROBIAL AND/OR REPARATIVE DENTIN STIMULATING DENTAL COMPOSITIONS AND METHODS FOR FORMING AND USING SUCH COMPOSITIONS

BACKGROUND OF THE INVENTION

1. The Field of the Invention

The application is directed to compositions and methods for forming dental compositions. More particularly, the compositions and methods are directed to dental compositions which have adhesive, antimicrobial and/or reparative dentin stimulating properties. These compositions are primarily useful as pulp caps and liners.

2. The Relevant Technology

Conventional dentin liners and pulp caps provide several advantageous properties which make these dentin liners and pulp caps useful in restorative dentistry. However, these useful properties cannot be reliably obtained.

Conventional dental liners are used to line a preparation made in a tooth after a cavity has been excavated in order to receive a filling material, particularly when the preparation penetrates beyond the enamel and deeply into the dentin. Dental liners are utilized before application of a filling material to act as a barrier against ingress of bacteria which can cause decay, to stimulate reparative dentin and/or to provide thermal insulation.

Dental liners can be used with any type of filling material; although, bonded composite fillings typically form a relatively solid seal so it is generally not necessary to use dental liners with composite fillings unless the preparation extends into a pulpal exposure or is near a pulpal exposure. Dental liners are, however, generally needed with metal amalgam fillings since metal amalgam fillings typically fail to seal the exposed interior of the tooth from accessibility by bacteria, to stimulate reparative dentin and/or to provide thermal insulation.

The same dental material utilized for liners is also conventionally utilized for pulp capping to protect the pulp after excavating deep caries which result in penetration near or into the pulp chamber. The pulp and the adjacent tissue, the pink dentin, are the living portion of a tooth and accordingly are highly sensitive. A failure to properly seal the pulp chamber can potentiate bacteria to infect the pulp. Since the infected area is in a hard and rigid tooth, the infected area cannot expand with the inflammation caused by the infection which causes the blood flow to the infected area to be restricted. As a result of the blood supply being restricted, the ability of the pulp to fight off the infection is compromised which generally causes the tooth to die. Accordingly, it is crucial to protect the pulp from infection by utilizing a pulp cap as a barrier against ingress of bacteria and/or to initiate reparative bridge formation for a biological seal.

In addition to sealing the pulp cavity to prevent ingress from bacteria, it is also important to stimulate reparative bridge formation as quickly as possible. Accordingly, pulp capping compositions are preferred which can also stimulate dentin repair when a pulp exposure or near pulp exposure occurs. To increase the likelihood of reparative bridge formation, calcium hydroxide compositions are conventionally utilized. Calcium hydroxide compositions are also used since the high pH of the calcium hydroxide kills bacteria.

Exposure of the pulp often occurs as a result of excavating deep caries in preparation for placing a filling or crown. Restorative dental procedures related to fillings and crowns may require the use of harsh chemicals which can result in postoperative sensitivity if the chemicals contact the pulp. The steps for restorative dental procedures related to fillings and crowns if a deep preparation or exposure has been excavated, generally involve disinfecting the area with a disinfectant, drying the area, placing a pulp cap at or near the opening into the pulp chamber, etching the area, priming the area and then applying a bonding resin for a composite or crown or placing a metal amalgam filling. A properly applied pulp cap not only minimizes the likelihood and degree of postoperative sensitivity from chemicals or bacteria in the dentin tubules near or in the pulp but the postoperative inflammatory response is also reduced; hence healing and predictable nonendodontic success is facilitated.

Although, the survivability of a tooth having an exposed or nearly exposed pulp can be increased by the use of a pulp cap, conventional pulp caps generally fail to adequately seal a treated area and generally have a deleterious impact on the retention of restorations. Any conventional liner has a negative impact on a bonded restoration due primarily to the strength of the liner which is significantly less than that of the covering restorative material.

Glass ionomer cements have been taught as a sealing-type liner. Glass ionomer cements are two components systems comprising a liquid component such as polyacrylic acid and a powder component such as ion leaching glasses, which are mixed together. Unfortunately, calcium hydroxide is not compatible with the polyacrylic acid, as the polyacrylic acid reacts with calcium hydroxide to form a salt, thus inactivating the calcium hydroxide. Glass ionomer cements are also not compatible with disinfectant agents as the agents interfere with bonding. Additionally, glass ionomer cements are significantly weaker than composites or metals. When compared with composites, the strength of the bond adhesion to a tooth is much weaker as the bond can be no stronger than the strength of the weak glass ionomer liner material.

The most significant clinical concern of nonadhesive pulp caps and liners is that strong tooth treatment modality may cause tissue harm. For example, many conventional nonadhesive pulp caps and liners fail to form a seal and those that do form a seal frequently fail due to being dislodged by a dental tool, brush, etc. Additionally, shaping or contouring a composite or metal amalgam filling often causes weak liners to be displaced by the forces experienced during the procedure which yields a liner that is no longer an effective or reliable barrier. As a result, the usefulness of such nonadhesive pulp caps and liners is limited since the protective seal can be compromised by being merely bumped by a dental tool or by being dislodged during instrumented shaping or contouring.

Accordingly, despite the number of materials available to dental practitioners as pulpal protection materials and dentin liners, there is not a known material which provides a highly reliable seal against bacteria ingress and facilitates reparative dentin formation. Conventional liners and pulp caps typically comprise calcium hydroxide liquids formed from at least calcium hydroxide in conjunction with water-based nonpolymerizable materials and polymerizable nonadhesive materials. Examples of conventionally utilized water-based nonpolymerizable materials include calcium hydroxide and water, and usually thickening or gelling materials such as guar gum, xanthan gum, methylcellulose or polycarboxymethylene. The nonpolymerizable materials cause the compositions to be highly viscous and to have low adhesion strengths. Examples of conventionally utilized polymerizable nonadhesive materials include alkyl methacrylates and alkyl amino methacrylates. These polymerizable nonadhesive materials also fail to contribute the properties necessary to provide an effective and reliable seal. These materials are much weaker than the covering restorative materials and hence provide a weak foundation for the stronger definitive restorations.

Accordingly, it would be useful to have dentin liner and pulp capping compositions which provide an effective and reliable seal against ingress from microorganisms, which provide reparative dentin stimulative and which protect an area in a tooth from harsh chemicals used in typical dental restorative procedures.

It would also be useful to have dentin liner and pulp capping compositions which are stable as a one package paste that can be stored and then applied to a dental substrate as needed.

Finally, it would be useful to have dentin liner and pulp capping compositions which have a rheology that enable the compositions to be dispensed from a syringe.

SUMMARY AND OBJECTS OF THE INVENTION

It is an object of the present invention to provide dental compositions such as pulpal protection materials and dentin liners, which provide an effective and reliable seal against microbial ingress, which provide reparative dentin stimulation and which protect an area in a tooth from harsh chemicals used in typical dental restorative procedures and have strong physical properties.

It is another object of the present invention to provide compositions useful as dentin liners and pulp caps which are stable as a one package paste that can be stored and then applied to a dental substrate.

Finally, it is an object of the present invention to provide compositions that are useful as dentin liner and pulp cap compositions and which have a rheology that enable the compositions to be dispensed from a syringe.

The present invention features adhesive antimicrobial and/or reparative dentin stimulating dental compositions and methods for forming and using such compositions. The compositions are primarily useful as pulp caps and dentin liners. The composition comprises at least an alkyl methacrylate having an oxyphosphorus group, a polymerization initiator and an antimicrobial agent. In addition to eliminating microorganisms, the antimicrobial agent can also provide reparative dentin stimulation. The composition may also comprise other additives such as fillers and diluent monomers.

A primary advantage of the adhesive antimicrobial dental compositions include their usefulness as pulp caps and dentin liners which eliminate microorganisms in the treated area and which provide an effective and reliable seal against microbial ingress. Additionally, the antimicrobial agent is not consumed during the polymerization reaction and is capable of antimicrobial activity even after polymerization. The compositions also provide reparative dentin stimulation and protect an area in a tooth from harsh chemicals used in typical dental restorative procedures. The compositions have physical properties comparable to the definitive restorations.

Another advantage of the compositions includes stability during storage and the ability to be polymerized in situ upon initiation of the photoinitiator.

Finally, another advantage of the compositions includes a rheology and viscosity that enables the composition to be delivered onto a substrate from a syringe.

These and other objects, features and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings listed hereinbelow.

DETAILED DESCRIPTION OF THE PREFERRED EMBODIMENTS

Figure 1:
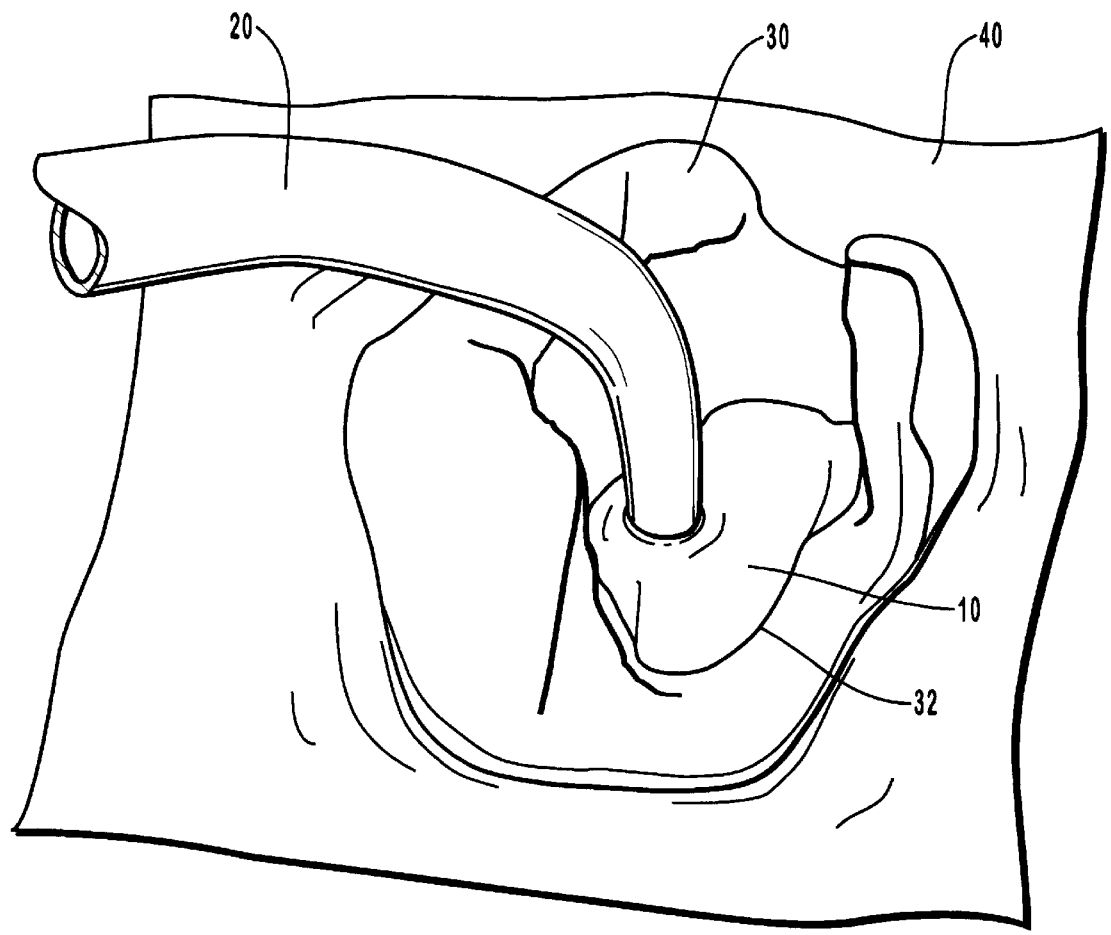
FIG. 1 is perspective view of an adhesive antimicrobial dental composition being expressed from a syringe tip onto the dentin of a tooth which is shown isolated by a rubber dam.

The adhesive antimicrobial and/or reparative dental compositions and methods for forming and using such compositions provide significant advantages over conventional dental compositions used as liners, pulp caps, base materials, etc. The compositions comprise at least one alkyl methacrylate having at least one oxyphosphorus group, an antimicrobial agent and a curing agent. The compositions also optionally further comprise other monomers, fillers, radio opaques and other constituents as necessary to achieve particular properties.

The compositions are effective in sealing the treated substrate from ingress by bacteria and killing bacteria within the treated and sealed area. By providing an effective and reliable seal, the substantial irritation or increased sensitivity is avoided that occurs when conventional liners and pulp caps leak. Additionally, high physical strength properties are obtained. The composition also enable resin based filling materials, such as composites and resin luting agents, to intimately and chemically bond.

A. Adhesion Monomers

Polymerizable adhesion monomers comprising at least one alkyl methacrylate having at least one oxyphosphorus group are utilized in the compositions of the present invention. These oxyphosphorus alkyl methacrylates provide adhesion strengths adequate to form an effective and reliable seal. Due primarily to the use of these oxyphosphorus alkyl methacrylates, the compositions can form a seal without risk of failure due to being bumped by a dental tool or by being dislodged during instrumented shaping or contouring. After the dental procedures are completed, the compositions continue to be an effective back-up seal against ingress from microorganisms.

Additionally, these adhesion monomers are stable in the presence of the polymerization initiator, the antimicrobial agent and the other additives such as fillers. Accordingly, the compositions are characterized as being capable of being polymerized in situ by initiation of the polymerization initiator after the composition is placed in contact with the substrate.

The stability enables the compositions to be utilized as a single component system or a one package composition and to be stable until polymerization is intentionally initiated.

More specifically, the composition is formed from constituents that once mixed thereafter form a stable composition that is ready for storage and subsequent application directly to a substrate for in situ polymerization. The primary advantage of such a system is increased efficiency for the dental practitioner. After the composition is mixed, it preferably maintains its capabilities to polymerize and to be utilized to counteract antimicrobial activity for at least about six months, more preferably at least about a year and most preferably at least about two years.

The most preferred oxyphosphorus alkyl methacrylate is bis glycerol methacrylate phosphate. Examples of other preferred oxyphosphorus alkyl methacrylates include: bis 2-hydroxy ethyl methacrylate phsophate, phosphate ester of p-hydroxyphenyl methacrylamide, phosphate ester of 3-hydroxy propyl methacrylate, and phosphate ester of 4-hydroxy butyl methacrylate. The oxyphosphorus alkyl methacrylate can be any alkyl methacrylate having an oxyphosphorus group or phosphorus acid group selected from the group consisting of:

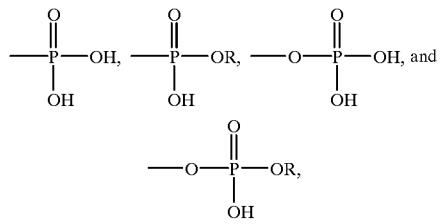

wherein R is an alkyl. The phosphorus alkyl methacrylates are preferably essentially nonreactive with the antimicrobial agents. Mixtures and derivatives of any of the above oxyphosphorus alkyl methacrylates are also within the scope of the invention. In addition to the above oxyphosphorus alkyl methacrylates, other oxyphosphorus alkyl methacrylates are within the contemplation of the present invention and can be found by routine experimentation by reading the disclosure and practicing the invention.

The oxyphosphorus alkyl methacrylates of the present invention are provided in a concentration ranging from about 0.01 to about 90 percent, preferably from about 0.5 to about 30 percent, and most preferably from about 1 to about 12 percent by weight of the composition.

B. Antimicrobial and/or Dentin Reparative Facilitating Agents

The inventive compositions contain antimicrobial agents that eliminate microorganisms through contact when the composition is placed on the dental substrate and also continue to eliminate microorganisms even after polymerization. The primary advantages of killing microorganisms, such as bacteria, is that the pulp can heal and form a reparative bridge.

An adhesive antimicrobial dental composition always provides optimal antimicrobial activity since the agents are not impeded by being in the mixture, are not consumed by the polymerization reaction and are not substantially inhibited after polymerization of the monomers. Additionally, some of these agents can act as dentin reparative facilitating agents which stimulate bridge formation.

Examples of antibacterial agents that can be utilized to prevent ingress by microorganisms and to kill microorganisms on the area being treated by the composition include: organohalogens, antibiotics, alkali metal hydroxides, alkaline earth metal oxides and alkaline earth metal hydroxides. Examples of antibacterial organohalogens include: 1,1'-hexamethylene bis(5(p-chlorophenyl)biguanide), cetyl pyridinium chloride, benzalkonium chloride and cetyl pyridinium bromide. Examples of suitable antibiotics include: 4'-sulfamoylsulfanilanilide, 3-amino-6-(2-(5-nitro-2-furyl) vinyl)pyridiazine, transpseudomonic acid, xanthomycin, alpha-amino-p-toluene sulfonamide, alpha-azido benzyl penicillin, penicillin O, penicillin N, monopropionyl erthromycin and erythromycin 9(O-((2-methoxy ethoxy)methyl) oxime. Examples of suitable alkali metal hydroxides include sodium hydroxide and lithium hydroxide. Examples of suitable alkaline earth metal oxides include: calcium oxide, magnesium oxide, barium oxide, and strontium oxide. Examples of suitable alkaline earth metal hydroxides include: calcium hydroxide, magnesium hydroxide, barium hydroxide, and strontium hydroxide.

The preferred antimicrobial agent is calcium hydroxide since calcium hydroxide not only kills microorganisms but also enhances or promotes reparative bridge formation. The reparative bridge formation dramatically increase the likelihood that a tooth that has had its pulp and/or the adjacent pink dentin exposed with survive and continue to be viable. Regardless of the antimicrobial agent utilized, the agent preferably has sufficient antimicrobial ability after polymerization of the oxyphosphorus alkyl methacrylate to prevent ingress by microorganisms into an area treated with the composition and to kill on contact any microorganisms that were sealed into the treated area.

The antimicrobial initiators of the present invention are provided in a concentration ranging from about 0.001 to about 80 percent, preferably from about 0.005 to about 45 percent, and most preferably from about 0.01 to about 35 percent by weight of the composition.

C. Initiators

Initiators are provided in the composition to induce polymerization of the monomer. The initiators or curing agents comprise radiant energy polymerization initiators with or without an appropriate organic amine additive or a peroxide and an appropriate organic amine additive. Curing agents may be selected to be complementary to other ingredients for a selected dental procedure.

Examples of photoinitiators include camphorquinone; benzoin methyl ether; 2-hydroxy-2-methyl-1-phenyl-1-propanone; diphenyl 2,4,6-trimethylbenzoyl phosphine oxide; benzoin ethyl ether; benzophenone; 9,10-anthraquinone, and equivalents.

Examples of peroxides include benzoyl peroxide, 2-butanone peroxide, lauroyl peroxide and tert-butyl peroxide.

Optional additives such as amine additives are preferred in formulating curing agents to assist the curing agents depending upon the specific application of the composition. Examples of amine additives include dimethyl amino ethyl methacrylate; tri ethyl amine; 2-dimethylamino ethanol; diethyl amino ethyl methacrylate; trihexyl amine; N,N-dimethyl-p-toluidine; N-methylethyanolamine, 2,2'(p-tolyimino)diethanol and equivalents.

The curing agents of the present invention are provided in a concentration ranging from about 0.05 to about 5 percent, preferably from about 0.1 to about 2 percent, more preferably from about 0.2 to about 1 percent. In addition to the above curing agents, other curing agents are within the contemplation of the present invention and can be found by routine experimentation by reading the disclosure and practicing the invention.

D. Fillers

Fillers can also be added as necessary to function for examples as visible light opaquers and radio-opaquers. The fillers utilized in the dental compositions of the present invention are not consumed by the polymerization reaction. Accordingly, the concentration of the fillers after being intermixed in the composition remains essentially constant compared to the concentration of the fillers after polymerization of the monomers as does the concentration of the antibacterial agents.

Examples of suitable inorganic fillers include silicon dioxide, titanium dioxide, barium sulfate, strontium sulfate, barium chloride, strontium chloride and calcium phosphate tribasic. The fillers are added to provide radiopacity, minimize polymerization shrinkage and to reduce the total heat potential of polymerization.

The fillers of the present invention are provided in a concentration ranging up to about 85 percent, preferably from about 2 to about 70 percent, and most preferably from about 5 to about 50 percent by weight of the composition.

E. Additional Monomers

Additional monomers, such as diluent monomers, can also be added to impact various properties such as viscosity. Examples of suitable additional monomers include alkyl methacrylates, alkyl hydroxy methacrylates and alkyl amino methacrylates. Examples of suitable alkyl methacrylates include triethylene glycol dimethacrylate, poly ethylene glycol dimethacrylate, butane diol dimethacrylate. Examples of suitable alkyl hydroxy methacrylates include 2-hydroxy ethyl methacrylate and glycerol dimethacrylate. Another suitable monomer includes Bis-GMA (bisphenol-A-diglycidyl dimethacrylate). An example of a suitable alkyl amino methacrylate includes urethane dimethacrylate.

The additional monomers of the present invention are provided in a concentration ranging up to about 90 percent, preferably from about 5 to about 80 percent, and most preferably from about 10 to about 70 percent by weight of the composition.

F. Methods of Use

The inventive adhesive antimicrobial dental compositions is made in a paste or gel form that is rheologically able to be expressed from a dental syringe. The components of the composition form either an emulsion, suspension, dispersion, solution, etc. depending upon selection of a preferred application.

The inventive composition is applied by any of several methods. FIG. 1 is a perspective view of a composition 10 being expressed from a syringe tip 20 into an exposure 32 onto the dentin of a tooth 30. Tooth 30 is shown isolated by a rubber dam 40. Composition 10 is applied as layer which is just adequate in size to ensure that the composition will form an effective and reliable barrier. The composition is then polymerized.

One embodiment of the adhesive antimicrobial dental composition comprises: 10.0% antimicrobial and dentin reparative facilitating agent (calcium hydroxide), 5.0% phosphated methacrylates (bis-glycerol methacrylate phosphate), 63.0% methacrylates (57.0% urethane dimethacrylate and 6.0% triethylene glycol dimethacrylate), 11.0% fillers (1.0% titanium dioxide and 10.0% calcium phosphate tribasic), 0.7% polymerization initiator (0.5% dimethyl amino ethyl methacrylate and 0.2% camphoroquinone), and 10.3% radio opaques (barium sulfate). The primary advantage of the composition is the formation of an effective and reliable seal. As a result, the seal is not compromised during dental procedures. Additionally, the composition protects dentin from etchant if used close to pulp. Some other advantages of this composition include: the ability to be light cured in 20 seconds at a thickness of 2 mm, the ability to be syringe dispensed radiopacity, and the ability to bond to composites or various dentin bonding systems.

EXAMPLES OF THE PREFERRED EMBODIMENTS

Several examples of the present invention are presented as merely illustrative of some embodiments of the present invention. These examples are not to be construed as limiting the spirit and scope of the invention.

Example 1 is a comparative example using a pull test to identify the tensile strength of a polymerizable calcium hydroxide paste without an oxyphosphorus alkyl methacrylate. Example 2 identified the tensile strength of a composition of the present invention by a pull test for comparison with the results in Example 1.

Examples 3–8 are hypothetical examples produced in furtherance of reducing the present invention to practice. All amounts are given in weight percent.

Example 1

The tensile strength or adhesiveness was tested of a bond formed by cementing a crown onto a tooth without the adhesive antimicrobial dental composition of the present invention. The tests were all conducted in a manner that measured the strength of the bond between a tooth and a crown, as a function of chemical adhesion and not the degree of mechanical retention.

In each test, teeth were machined at a grinding angle of 16.5° to produce a 33° taper. From each machined tooth a mold was made and a tight fitting crown prepared from the mold. The 33° taper provided test data that reflects the strength of the bond interface as opposed to more parallel preparation which can cause the tooth to fracture and yield test data that reflects the strength of the tooth and not the bond interface.

A calcium hydroxide paste sold by Ultradent Products, Inc. as Ultra-Blend® base and liner was applied to a tooth and then light cured for 20 seconds. A crown was then seated over the tooth after application of resin-based cement sold as PermaLute® also from Ultradent Products, Inc. The PermaLute® cement cured in about four minutes.

After aging for 24 hours, the crown and the teeth were subjected to a tensile pull test at a speed of a 1 mm/min. The force required to break the bond between the tooth and the crown was measured by recording the load necessary to pull apart the tooth and crown. The results of the test for the tested samples were: 11.7 kg, 7.39 kg, 5.90 kg, 4.54 kg, 3.36 kg, 2.90 kg, 0.86 kg, 0.73 kg, 0.36 kg. The average was 4.19 kg with a standard deviation of 3.49 kg.

Example 2

In this example, an adhesive antimicrobial dental composition was formed having the following composition:

| Component | Percent by Weight of the Mixture |
| --- | --- |
| calcium hydroxide | 10.0% |
| bis-glycerol methacrylate phosphate | 5.0% |
| urethane dimethacrylate | 57.0% |
| triethylene glycol dimethacrylate | 6.0% |
| titanium dioxide | 1.0% |
| calcium phosphate tribasic | 10.0% |

-continued

| Component | Percent by Weight of the Mixture |
|---|---|
| dimethyl amino ethyl methacrylate | 0.5% |
| camphorquinone | 0.2% |
| barium sulfate | 10.3% |

The procedure outlined in Example 1 was used to test the tensile or adhesive strength of a bond when an adhesive antimicrobial dental composition was utilized. Mechanical anchoring was minimized and the experiments tested primarily the adhesive bond strength as a result of machining the tooth to produce a 33° taper. The composition was applied onto a tapered tooth and then light cured for 20 seconds. A crown was then seated over the tooth after application of a resin-based cement sold as PermaLute® also from Ultradent Products, Inc. The PermaLute® cement cured in about four minutes.

After aging for 24 hours, the tensile strength was measured by the same method as in Example 1. The results of the tested samples were: 21.32 kg, 17.37 kg, 9.305 kg, 17.32 kg, 13.79 kg, and 16.24 kg. The average was 15.89 kg with a standard deviation of 3.69 kg.

The average strengths of the bond interfaces for the teeth treated in Example 1 and Example 2, which were respectively 4.19 kg and 15.89 kg, indicates that the use of oxyphosphorus alkyl methacrylates significantly increases the tensile strength of a bond between a tooth and crown.

Example 3

In this example, an adhesive antimicrobial dental composition is formed having the following composition:

| Component | Percent by Weight of the Mixture |
|---|---|
| bis 2-hydroxy ethyl methacrylate | 10.0% |
| barium hydroxide | 25.0% |
| calcium phosphate tribasic | 5.0% |
| benzoin ethyl ether | 0.4% |
| N-methylethanol amine | 0.5% |
| glycerol dimethacrylate | 59.1% |

The adhesive antimicrobial dental composition would be expected to provide a better seal than liners or pulp caps which do not include phosphate metharylates. The composition would also be expected to seal a treated area to eliminate microorganisms in the treated area. The antimicrobial agent would not be expected to be consumed during the polymerization reaction and would be expected to be capable of antimicrobial activity even after polymerization.

Example 4

In this example, an adhesive antimicrobial dental composition is formed having the following composition:

| Component | Percent by Weight of the Mixture |
|---|---|
| strontium oxide | 30.0% |
| camphorquinone | 0.5% |
| diethyl amino ethyl methacrylate | 0.5% |
| bis glyceryl methacrylate phosphate | 69.0% |

The adhesive antimicrobial dental composition would be expected to provide a better seal than liners or pulp caps which do not include phosphate methacrylates. The composition would also be expected to seal a treated area to eliminate microorganisms in the treated area. The antimicrobial agent would not be expected to be consumed during the polymerization reaction and would be expected to be capable of antimicrobial activity even after polymerization.

Example 5

In this example, an adhesive antimicrobial dental composition is formed having the following composition:

| Component | Percent by Weight of the Mixture |
|---|---|
| cetyl pyridinium chloride | 4.0% |
| strontium chloride | 10.0% |
| 2-hydroxy-2-methyl-1-phenyl-1-propanone | 0.5% |
| diphenyl 2,4,6-trimethylbenzoyl phosphine oxide | 0.5% |
| xanthomycin | 1.0% |
| phosphate ester of 4-hydroxy butyl methacrylate | 29.0% |
| butane diol dimethacrylate | 55.0% |

The adhesive antimicrobial dental composition would be expected to provide a better seal than liners or pulp caps which do not include phosphate methacrylates. The composition would also be expected to be stable during storage and capable of in situ polymerization upon initiation of the photoinitiator. The composition would also be expected to seal a treated area to eliminate microorganisms in the treated area. The antimicrobial agent would not be expected to be consumed during the polymerization reaction and would be expected to be capable of antimicrobial activity even after polymerization.

Example 6

In this example, an adhesive antimicrobial dental composition is formed having the following composition:

| Component | Percent by Weight of the Mixture |
|---|---|
| penicillin N | 3.5% |
| silicon dioxide fumed | 16.0% |
| bis-glyceryl methacrylate phosphate | 3.0% |
| benzophenone | 1.0% |
| tri hexyl amine | 1.5% |
| calcium phosphate tribasic | 10.0% |
| bis 2-hydroxy ethyl methacrylate | 4.0% |
| triethylene glycol dimethacrylate | 61.0% |

The adhesive antimicrobial dental composition would be expected to provide a better seal than liners or pulp caps which do not include phosphate methacrylates. The composition would also be expected to be stable during storage and capable of in situ polymerization upon initiation of the photoinitiator. The composition would also be expected to seal a treated area to eliminate microorganisms in the treated area. The antimicrobial agent would not be expected to be consumed during the polymerization reaction and would be expected to be capable of antimicrobial activity even after polymerization.

Example 7

In this example, an adhesive antimicrobial dental composition is formed having the following composition:

| Component | Percent by Weight of the Mixture |
| --- | --- |
| 4'-sulfamoylsulfanilanilide | 1.0% |
| 1, 1'-hexamethylene bis (5(p-chlorophenyl) biguanide) | 1.0% |
| phosphate ester of 3-hydroxy propyl methacrylate | 5.0% |
| urethane dimethacrylate | 92.0% |
| benzoin ethyl ether | 1.0% |
| 2-dimethylaminoethanol | 1.0% |

The adhesive antimicrobial dental composition would be expected to provide a better seal than liners or pulp caps which do not include phosphate methacrylates. The composition would also be expected to be stable during storage and capable of in situ polymerization upon initiation of the photoinitiator. The composition would also be expected to seal a treated area to eliminate microorganisms in the treated area. The antimicrobial agent would not be expected to be consumed during the polymerization reaction and would be expected to be capable of antimicrobial activity even after polymerization.

Example 8

In this example, an adhesive antimicrobial dental composition is formed having the following composition:

| Component | Percent by Weight of the Mixture |
| --- | --- |
| magnesium oxide | 15.0% |
| barium chloride | 40.0% |
| 9, 10-anthraquinone | 0.9% |
| triethylamine | 0.3% |
| bis glyceryl methacrylate phosphate | 43.8% |

The adhesive antimicrobial dental composition would be expected to provide a better seal than liners or pulp caps which do not include phosphate methacrylates. The composition would also be expected to be stable during storage and capable of in situ polymerization upon initiation of the photoinitiator. The composition would also be expected to seal a treated area to eliminate microorganisms in the treated area. The antimicrobial agent would not be expected to be consumed during the polymerization reaction and would be expected to be capable of antimicrobial activity even after polymerization.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An adhesive antimicrobial dental composition comprising:

at least one alkyl methacrylate having at least one oxyphosphorus group having a formula selected from the group consisting of

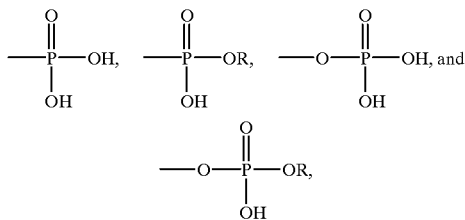

wherein R is an alkyl;

at least one additional monomer which is at least one of an alkyl methacrylate, an alkyl hydroxy methacrylate, an alkyl amino methacrylate, or bisphenol-A-diglycidyl dimethacrylate;

at least one polymerization photoinitiator which only initiates polymerization of the alkyl methacrylate having at least one oxyphosphorus group and the at least one additional monomer upon irradiating the dental composition with radiant energy, wherein the photoinitiator is at least one of camphorquinone, benzoin methyl ether, 2-hydroxy-2-methyl-1-phenyl-1-propanone, diphenyl-2,4,6-trimethylbenzoyl phosphine oxide, benzoin ethyl ether, benzophenone, or 9,10-anthroquinone;

a filler which is at least one of silicon dioxide, titanium dioxide, barium sulfate, strontium sulfate, barium chloride, strontium chloride, or calcium phosphate tribasic; and at least one antimicrobial agent in an antimicrobially effective amount, wherein the antimicrobial agent is at least one of an antibiotic, 1,1'-hexamethylene bis(5(p-chlorophenyl)biguanide), cetyl pyridinium chloride, benzalkonium chloride, cetyl pyridinium bromide, an alkali metal hydroxide, an alkaline earth metal hydroxide, or an alkaline earth metal oxide included in a form that permits formation of an alkaline earth metal hydroxide when the dental composition is exposed to water, wherein the dental composition is capable of being placed on a treatment area of a dental substrate for in situ polymerization of the alkyl methyacrylate by irradiating the dental composition with radiant energy for adherence to the dental substrate.

2. An adhesive antimicrobial dental composition as defined in claim 1, wherein the dental composition is capable of being stored and then delivered onto a dental substrate using a syringe.

3. An adhesive antimicrobial dental composition as defined in claim 1, wherein the alkyl methacrylate is selected from the group consisting of bis 2-hydroxy ethyl methacrylate phosphate, phosphate ester of p-hydroxyphenyl methacrylamide, phosphate ester of 3-hydroxy propyl metharylate, phosphate ester of 4-hydroxy butyl methacrylate, and mixtures of the foregoing.

4. An adhesive antimicrobial dental composition as defined in claim 1, wherein the alkyl methacrylate includes bis glycerol methacrylate phosphate.

5. An adhesive antimicrobial dental composition as defined in claim 1, wherein the alkyl methacrylate has a concentration in a range from about 0.01% to about 90% by weight of the dental composition.

6. An adhesive antimicrobial dental composition as defined in claim 1, wherein the composition maintains a seal after being polymerized in a preparation excavated in a tooth.

7. An adhesive antimicrobial dental composition comprising:
at least one alkyl methacrylate having at least one oxyphosphorus group having a formula selected from the group consisting of

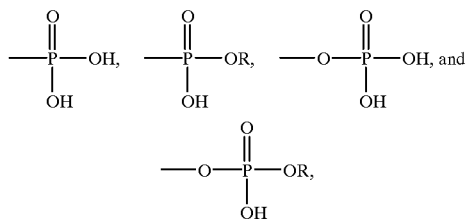

wherein R is an alkyl;
at least one additional monomer which is at least one of an alkyl methacrylate, an alkyl hydroxy methacrylate, an alkyl amino methacrylate, or bisphenol-A-diglycidyl dimethacrylate;
at least one polymerization photoinitiator which only initiates polymerization of the alkyl methacrylate having at least one oxyphosphorus group and the at least one additional monomer upon irradiating the dental composition with radiant energy, wherein the photoinitiator is at least one of camphorquinone, benzoin methyl ether, 2-hydroxy-2-methyl-1-phenyl-1-propanone, diphenyl-2,4,6-trimethylbenzoyl phosphine oxide, benzoin ethyl ether, benzophenone, or 9,10-anthroquinone;
a filler which is at least one of silicon dioxide, titanium dioxide, barium sulfate, strontium sulfate, barium chloride, strontium chloride, or calcium phosphate tribasic; and
calcium hydroxide in an antimicrobially effective amount,
wherein the dental composition is capable of being placed on a treatment area of a dental substrate for in situ polymerization of the alkyl methyacrylate by irradiating the dental composition with radiant energy.

8. An adhesive antimicrobial dental composition comprising:
at least one alkyl methacrylate having at least one oxyphosphorus group having a formula selected from the group consisting of

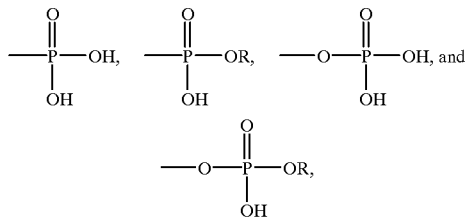

wherein R is an alkyl, and wherein the alkyl methacrylate is selected from the group consisting of bis glycerol methacrylate phosphate, bis 2-hydroxy ethyl methacrylate phosphate, phsophate ester of p-hydroxyphenyl methacrylamide, phosphate ether of 3-hydroxy propyl methacrylate, phosphate ester of 4-hydroxy butyl methacrylate, and mixtures of the foregoing;
at least one additional monomer which is at least one of an alkyl methacrylate, an alkyl hydroxy methacrylate, an alkyl amino methacrylate, or bisphenol-A-diglycidyl dimethacrylate;
at least one polymerization photoinitiator which only initiates polymerization of the alkyl methacrylate having at least one oxyphosphorus group and the at least one additional monomer upon irradiating the dental composition with radiant energy, wherein the photoinitiator is at least one of camphorquinone, benzoin methyl ether, 2-hydroxy-2-methyl-1-phenyl-1-propanone, diphenyl-2,4,6-trimethylbenzoyl phosphine oxide, benzoin ethyl ether, benzophenone, or 9,10-anthroquinone;
a filler which is at least one of silicon dioxide, titanium dioxide, barium sulfate, strontium sulfate, barium chloride, strontium chloride, or calcium phosphate tribasic; and
at least one antimicrobial agent in an antimicrobially effective amount, wherein the antimicrobial agent is at least one of an antibiotic, 1,1'-hexamethylene bis(5(p-chlorophenyl)biguanide), cetyl pyridinium chloride, benzalkonium chloride, cetyl pyridinium bromide, an alkali metal hydroxide, an alkaline earth metal hydroxide, or an alkaline earth metal oxide included in a form that permits formation of an alkaline earth metal hydroxide when the dental composition is exposed to water,
wherein the dental composition is capable of being placed on a treatment area of a dental substrate for in situ polymerization of the alkyl methyacrylate by irradiating the dental composition with radiant energy.

9. An adhesive antimicrobial dental composition comprising:
at least one alkyl methacrylate having at least one oxyphosphorus group with a formula selected from the group consisting of:

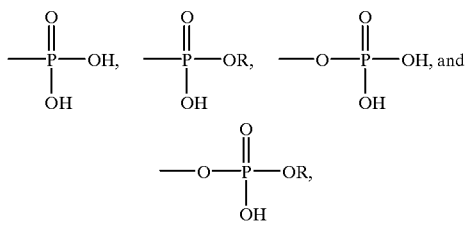

wherein R is an alkyl; and wherein the alkyl methacrylate is selected from the group consisting of bis glycerol methacrylate phosphate, bis 2-hydroxy ethyl methacrylate phosphate, phsophate ester of p-hydroxyphenyl methacrylamide, phosphate ether of 3-hydroxy propyl methacrylate, phosphate ester of 4-hydroxy butyl methacrylate, and mixtures of the foregoing;
at least one additional monomer which is at least one of an alkyl methacrylate, an alkyl hydroxy methacrylate, an alkyl amino methacrylate, or bisphenol-A-diglycidyl dimethacrylate;
at least one polymerization photoinitiator which only initiates polymerization of the alkyl methacrylate having at least one oxyphosphorus group and the at least one additional monomer upon irradiating the dental composition with radiant energy, wherein the photoinitiator is at least one of camphorquinone, benzoin methyl ether, 2-hydroxy-2-methyl-1-phenyl-1-propanone, diphenyl-2,4,6-trimethylbenzoyl phosphine oxide, benzoin ethyl ether, benzophenone, or 9,10-anthroquinone;

a filler which is at least one of silicon dioxide, titanium dioxide, barium sulfate, strontium sulfate, barium chloride, strontium chloride, or calcium phosphate tribasic; and calcium hydroxide in a concentration ranging from about 0.005% to about 45% by weight of the dental composition, wherein the dental composition is capable of being placed on a treatment area of a dental substrate for in situ polymerization of the alkyl methyacrylate by irradiating the dental composition with radiant energy for adherence to the dental substrate.

10. An adhesive antimicrobial dental composition as defined in claim 1, wherein the alkali metal hydroxide is selected from the group consisting of sodium hydroxide, lithium hydroxide, and mixtures thereof.

11. An adhesive antimicrobial dental composition as defined in claim 1, wherein the alkaline earth metal oxide is selected from the group consisting of calcium oxide, magnesium oxide, barium oxide, strontium oxide, and mixtures thereof.

12. An adhesive antimicrobial dental composition as defined in claim 1, wherein the alkaline earth metal hydroxide is selected from the group consisting of magnesium hydroxide, barium hydroxide, strontium hydroxide, and mixtures thereof.

13. An adhesive antimicrobial dental composition as defined in claim 1, wherein the alkaline earth metal hydroxide is calcium hydroxide.

14. An adhesive antimicrobial dental composition as defined in claim 1, wherein the antimicrobial agent has a concentration in a range from about 0.001% to about 80% by weight of the dental composition.

15. A method of manufacturing a syringe-deliverable adhesive antimicrobial dental composition capable of being applied to a dental substrate by means of a syringe and polymerized in situ, the method comprising the steps of:

(a) forming an adhesive antimicrobial dental composition by mixing together;

at least one alkyl methacrylate having at least one oxyphosphorus group having a formula selected from the group consisting of

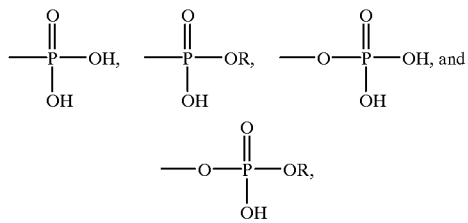

wherein R is an alkyl;

at least one additional monomer which is at least one of an alkyl methacrylate, an alkyl hydroxy methacrylate, an alkyl amino methacrylate, or bisphenol-A-diglycidyl dimethacrylate;

at least one polymerization photoinitiator which only initiates polymerization of the alkyl methacrylate having at least one oxyphosphorus group and the at least one additional monomer upon irradiating the dental composition with radiant energy, wherein the photoinitiator is at least one of camphorquinone, benzoin methyl ether, 2-hydroxy-2-methyl-1-phenyl-1-propanone, diphenyl-2,4,6-trimethylbenzoyl phosphine oxide, benzoin ethyl ether, benzophenone, or 9,10-anthroquinone;

a filler which is at least one of silicon dioxide, titanium dioxide, barium sulfate, strontium sulfate, barium chloride, strontium chloride, or calcium phosphate tribasic; and at least one antimicrobial agent in an antimicrobially effective amount, wherein the antimicrobial agent is at least one of an antibiotic, 1,1'-hexamethylene bis(5(p-chlorophenyl)biguanide), cetyl pyridinium chloride, benzalkonium chloride, cetyl pyridinium bromide, an alkali metal hydroxide, an alkaline earth metal hydroxide, or an alkaline earth metal oxide included in a form that permits formation of an alkaline earth metal hydroxide when the dental composition is exposed to water; and (b) introducing the adhesive antimicrobial dental composition into a syringe.

16. A method for treating a dental substrate with an adhesive antimicrobial dental composition comprising the steps of:

(a) providing an adhesive antimicrobial dental composition comprising:

at least one alkyl methacrylate having at least one oxyphosphorus group having a formula selected from the group consisting of

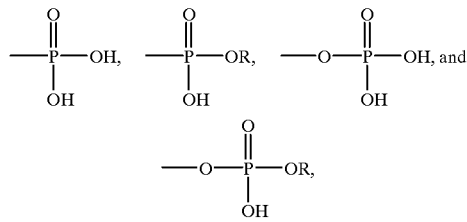

wherein R is an alkyl;

at least one additional monomer which is at least one of an alkyl methacrylate, an alkyl hydroxy methacrylate, an alkyl amino methacrylate, or bisphenol-A-diglycidyl dimethacrylate;

at least one polymerization photoinitiator which only initiates polymerization of the alkyl methacrylate having at least one oxyphosphorus group and the at least one additional monomer upon irradiating the dental composition with radiant energy, wherein the photoinitiator is at least one of camphorquinone, benzoin methyl ether, 2-hydroxy-2-methyl-1-phenyl-1-propanone, diphenyl-2,4,6-trimethylbenzoyl phosphine oxide, benzoin ethyl ether, benzophenone, or 9,10-anthroquinone;

a filler which is at least one of silicon dioxide, titanium dioxide, barium sulfate, strontium sulfate, barium chloride, strontium chloride, or calcium phosphate tribasic; and at least one antimicrobial agent in an antimicrobially effective amount, wherein the antimicrobial agent is at least one of an antibiotic, 1,1'-hexamethylene bis(5(p-chlorophenyl)biguanide), cetyl pyridinium chloride, benzalkonium chloride, cetyl pyridinium bromide, an alkali metal hydroxide, an alkaline earth metal hydroxide, or an alkaline earth metal oxide included in a form that permits formation of an alkaline earth metal hydroxide when the dental composition is exposed to water;

(b) applying the dental composition to an area of the dental substrate; and (c) irradiating the applied dental composition with radiant energy in order to initiate polymerization of the alkyl methyacrylate.

* * * * *

UNITED STATES PATENT AND TRADEMARK OFFICE
CERTIFICATE OF CORRECTION

PATENT NO.   : 6,071,528
DATED        : June 6, 2000
INVENTOR(S)  : Steven D. Jensen It is certified that error appears in the above-identified patent and that said Letters Patent is hereby corrected as shown below:

Column 3,
Line 9, after "dentin" change "stimulative" to -- stimulation --

Column 6,
Line 21, after "exposed" change "with" to -- will --
Line 55, after "N-" change "methylethyanolamine" to -- methylethanolamine --

Column 7,
Line 47, after "as" and before "layer" insert -- a --

Column 8,
Line 41, after "of" and before "resin-based" insert -- a --

Column 9,
Line 50, after "phosphate" change "metharylates" to -- methacrylates --

Column 11,
Line 63, after "as" change "illustrated" to -- illustrative --

Column 12,
Line 63, before "phosphate" change "metharylate" to -- methacrylate --

Column 13,
Line 48, after "alkyl" change "methyacrylate" to -- methacrylate --

Signed and Sealed this

Twenty-fifth Day of September, 2001

*Attest:*

*Attesting Officer*

NICHOLAS P. GODICI
*Acting Director of the United States Patent and Trademark Office*